United States Patent
Hunt, Jr. et al.

(10) Patent No.: US 6,358,460 B1
(45) Date of Patent: Mar. 19, 2002

(54) METHOD FOR TIP FORMING PEELABLE PTFE TUBING

(75) Inventors: William E. Hunt, Jr., Jaffrey, NH (US); George Purtell, Westford, MA (US); Peter D. Spohn, Brookline, NH (US)

(73) Assignee: TFX Medical Incorporation, Jaffrey, NH (US)

( * ) Notice: Subject to any disclaimer, the term of this patent is extended or adjusted under 35 U.S.C. 154(b) by 0 days.

(21) Appl. No.: 09/472,329

(22) Filed: Dec. 23, 1999

(51) Int. Cl.[7] .......................... B29C 47/04; B29C 47/06
(52) U.S. Cl. .................. 264/491; 264/113; 264/119; 264/127; 264/171.26; 264/245; 264/296; 264/320
(58) Field of Search ................. 264/460, 491, 264/113, 119, 127, 245, 296, 320, 323, 241, 171.26

(56) References Cited

U.S. PATENT DOCUMENTS

| | | | |
|---|---|---|---|
| 3,861,972 A | | 1/1975 | Glover et al. |
| 4,404,159 A | | 9/1983 | McFarlane |
| 4,661,300 A | | 4/1987 | Daugherty |
| 4,753,765 A | | 6/1988 | Pande |
| 5,514,236 A | | 5/1996 | Avellanet et al. |
| 5,637,267 A | * | 6/1997 | Lo et al. ................ 264/80 |
| 5,985,195 A | * | 11/1999 | Muskatello ............. 264/161 |
| 6,086,970 A | * | 7/2000 | Ren ..................... 428/36.9 |
| 6,224,803 B1 | * | 5/2001 | Tiernan ................. 264/166 |

FOREIGN PATENT DOCUMENTS

EP     0 452 123 A1     4/1991

OTHER PUBLICATIONS

EPO Search Report.

* cited by examiner

Primary Examiner—Mary Lynn Theisen
(74) Attorney, Agent, or Firm—Peter F. Corless; Lisa Swiszcz Hazzard Edwards & Angell, LLP (57) ABSTRACT

Methods are disclosed for producing multi-layer peelable sheaths having formed tips, for use as medical introducer devices, e.g., sheaths for inserting a catheter or the like into a patient. The methods include the steps of preparing a first composition blend for forming an inner layer of the multi-layer sheath, preparing a second composition blend for forming an outermost layer of the multi-layer sheath, combining the first and the second composition blends into a multi-layer pre-form, processing the multi-layer pre-form for producing tubing, and forming a tip at one end of the tubing using a thermal process, thereby producing the multi-layer sheath having the inner layer, the outermost layer, and the formed tip. The methods of the present invention include adding a detectable material to the blend used for making the inner layer for facilitating external visualization of the multi-layer sheath, thereby achieving a sheath with a formed tip having no visible discoloration. The methods also incorporate a reduced sintering process for achieving an optimally cured, peelable sheath having excellent tear properties.

16 Claims, 4 Drawing Sheets

METHOD FOR TIP FORMING PEELABLE PTFE TUBING

BACKGROUND OF THE INVENTION

1. Field of the Invention

The present invention relates generally to tubular sheaths, and more particularly to tubular sheaths used for permitting percutaneus introduction of devices, e.g., a catheter, or the like, into a patient.

2. Background

Introducer sheaths are commonly used by medical personnel for permitting percutaneus insertion of devices such as catheters, or the like, into patients. Introducer sheaths advantageously allow medical personnel to insert such devices into vascular systems of patients without requiring invasive surgical procedures, thereby facilitating the use of such devices and minimizing the recovery time of the patient.

Various design configurations and processes for manufacturing have been used in the production of sheaths for medical applications. For example, in U.S. Pat. No. 4,306,562 (the '562 patent) issued Dec. 22, 1981, to Osborne, a flexible cannula is disclosed. In accordance with that disclosure, the flexible cannula comprises material which tears readily in a longitudinal direction and can thus be easily removed by pulling tabs on opposite sides of the cannula apart after the catheter or other device has been inserted into the body. The '562 patent further discloses that the cannula is disposed about a dilator having a distal end that is tapered for enlarging a puncture site to accommodate the cannula. Similarly, the cannula has a distal end where there is a slight taper to create an appropriately snug fit with the dilator and also to facilitate the enlarging of the puncture site to accommodate the cannula.

Moreover, the '562 patent discloses that the tapered distal end of the cannula is formed by measuring an appropriate length of tubing; applying a heat gun to the tubing; and, upon application of this heat, stretching the tubing, thereby yielding the tapered end. The tip is then cut at a point where the inside diameter of the cannula approximates the outside diameter of the dilator, which will be used with the particular cannula. The '562 patent discloses that the heat-formed tapered end of the cannula serves two purposes. First, it facilitates insertion of the cannula into the body. Second, a tight fit with a probe at this end minimizes blood loss.

In addition, in U.S. Pat. No. 4,581,025 (the '025 patent) issued Apr. 8, 1986, to Timmermans, a sheath is disclosed. In accordance with that disclosure, the sheath comprises a tubular structure formed of a flexible material that is compatible for insertion within the body and having proximal and distal ends. In one embodiment, the tubular structure includes one slit having an open and a closed end. The tubular structure is further comprised of a tab defined by the slit, whereby when the tab is pulled apart from any object extending through the lumen of the tubular structure, the tubular structure tears longitudinally removing the tubular structure from the object. In another embodiment, the tubular structure is cuffed between the closed end of the slit and the distal end of the tubular structure, the cuff defining the proximal end of the tubular structure. The cuff prevents the slit from tearing prematurely and further provides a blunt, smooth open end at the proximal end that permits closure thereof by thumb pressure only in order to temporarily block blood flow or air aspiration during use. The '025 patent further discloses that the distal portion of the sheath is provided with a rounded or tapered tip to ensure a desirably snug fit between a dilator and the sheath and facilitate smooth introduction of the sheath within the body.

Introducer sheaths have traditionally been made of thermoplastic materials, and various processes for manufacturing have been used with such thermoplastic materials. For example, in U.S. Pat. No. 5,139,407 (the '407 patent) issued Aug. 18, 1992, to Kim et al., an apparatus for reducing thermoplastic material compression mold cycle time is disclosed. In accordance with that disclosure, a thermoplastic sheet is placed between a pair of mold members each having a thermal insulator and a mating metal mold insert. Radio frequency (RF) energy is applied to the inserts to dielectrically heat and melt the thermoplastic sheet. The heated sheet is then deformed in a low-pressure press with the insulators. The insulators are then replaced with cool thermally conductive structures to shorten the cooling cycle time. The thermally conductive structures cool the sheet by pressing the sheet in a high-pressure press. The '407 patent further discloses that such thermoplastic materials include TEFLON™ polytetrafluoroethylene (PTFE), which is sold by and a trademark of the E.I. DuPont Co., Inc., Wilmington, Del., USA.

In addition, in U.S. Pat. No. 5,360,330 (the '330 patent) issued Nov. 1, 1994, a RF heated mold for thermoplastic materials is disclosed. In accordance with that disclosure, a source of RF energy is applied to a low thermal inertia heating element with high thermal conductivity, such as a spool, for rapidly heating the heating element to settable predetermined temperature, which temperature is maintained essentially constant. The heating element is detachably attached about the die of a mold for transferring heat to the die to form, mold, weld, or extrude thermoplastic material placed within the mold. Thermal chokes restrict heat transfer from the die to the remainder of the mold. One or more heat sinks draws and dissipates heat from the thermal chokes to maintain cool zones of the mold. Following the heating cycle, upon termination of application of RF energy to the spool, cooling may be accelerated by directing a stream of gas upon the heating element. The '330 patent further discloses a mold for the purpose of tapering an end of a thermoplastic sleeve, which is subsequently disposed about an intravenous catheter and is used for engaging the catheter with a vein of a patient. The tapered end of the thermoplastic sleeve facilitates sliding insertion of the end portion of the sleeve into the vein of the patient.

Although the various design configurations and manufacturing processes described above have been used in the production of introducer sheaths, we have recognized that forming tapered tips at the ends of introducer sheaths continues to be problematic, especially when introducer sheaths are made using preferred PTFE thermoplastic materials such as TEFLON™ PTFE. This is because PTFE thermoplastic materials generally have very high melting temperatures. Further, certain radiopaque substances, which are commonly added to the thermoplastic materials for facilitating x-ray or fluoroscopic visualization of the introducer sheaths, frequently cause discoloration of the introducer sheaths when the tapered tips are formed using heat or RF energy. As a result, processes for forming tapered tips of introducer sheaths that involve either heat or RF energy are often difficult to implement.

As an alternative to using heat or RF energy, tips of introducer sheaths may be tapered using a grinding process. However, introducer sheaths with formed tapered tips are generally regarded as being superior to introducer sheaths with ground tapered tips because the inner diameter of a formed tapered tip typically decreases around a forming mandrel, thereby resulting in an interference fit between the introducer sheath and a dilator disposed therein. This is advantageous when using the introducer sheath during the insertion of devices, e.g., a catheter, or the like, into a patient because there is essentially no gap between the sheath and the dilator that might get hung-up when the sheath and the dilator in combination penetrate the patient's skin or arterial/venous wall.

In contrast, because the inner diameter of a ground tapered tip typically does not decrease during the grinding process, it is very difficult to obtain a useful interference fit between an introducer sheath with a ground tip and a dilator disposed therein. This means that there is often a gap between the ground tip and the dilator that can get hung-up when penetrating the patient's skin or arterial/venous wall, thereby making the insertion of the introducer sheath into the patient unsuccessful.

Specifically, when an edge of the introducer sheath gets hung-up when penetrating the patient's skin or arterial/venous wall, a condition commonly known as "peel-back" frequently occurs. For example, during peel-back, the tapered tip of the introducer sheath typically distorts into an accordion-shape, thereby making sheath insertion virtually impossible. As a result, the distorted sheath/dilator set must be discarded, and another attempt must be made using a new sheath/dilator set. Not only is there a risk of potentially harming the patient's dermal and vascular systems during peel-back, but having to discard distorted sheath/dilator sets also substantially increases costs.

In addition, we have recognized that making an introducer sheath that is easily torn longitudinally, i.e., peelable, for removing the sheath from a device disposed therein is also problematic. For example, a conventional method for making a peelable introducer sheath includes mechanically skiving two (2) score lines on the outer surface of the introducer sheath, approximately 180° apart, that run longitudinally the entire length of the sheath. As a result, when the introducer sheath is split and peeled, the sheath tears in half along the two (2) score lines.

However, there are several variables that are known to affect the consistency and reliability of peelable introducer sheaths that are made according to this conventional method. For example, at the beginning of a production run, blades used to skive the outer surface of the introducer sheath are typically very sharp, but gradually become dull during the course of the production run. Such blade wear generally affects the quality of the score lines and therefore the consistency and reliability of the peel. Further, the blades are typically designed to cut to a predetermined depth. But, if, e.g., the wall thickness, the outer diameter, and/or the inner diameter of the sheath changes during the production run, then the cut depth may also change, thereby affecting the consistency and reliability of the peel.

It would therefore be desirable to have an introducer sheath with a formed tapered tip that is easy to manufacture and inexpensive to use. Such an introducer sheath would be made of preferred PTFE thermoplastic materials such as TEFLON™ PTFE. It would also be desirable to have an introducer sheath with a formed tapered tip that can be torn longitudinally, i.e., peelable, for easily removing the sheath from any device disposed therein.

SUMMARY OF THE INVENTION

The present invention provides a peelable introducer sheath with a formed tapered tip that is easy to manufacture and inexpensive to use. Specifically, manufacturing methods disclosed herein allow the production of introducer sheaths with thermally formed tapered tips that have no visible discoloration due to the thermal tip-forming process. Further, the introducer sheaths with formed tapered tips are externally visible during use by x-ray or fluoroscopic techniques. Still further, the introducer sheaths manufactured in accordance with the present invention allow straight and even peeling along the full length of the introducer sheaths.

According to one embodiment of the present invention, a method of manufacturing a multi-layer sheath, comprising the steps of preparing a first composition blend for forming an inner layer of the multi-layer sheath; preparing a second composition blend for forming an outermost layer of the multi-layer sheath; combining the first and the second composition blends into a multi-layer pre-form; processing the multi-layer pre-form for producing coherent tubing; and, forming a tip at one end of the coherent tubing using a thermal process, thereby producing the multi-layer sheath having the inner layer, the outermost layer, and the formed tip, wherein the method includes the substep of adding a detectable material to the first composition blend for facilitating external visualization of the multi-layer sheath.

According to another embodiment of the present invention, a method of manufacturing a multi-layer sheath, comprising the steps of preparing a first composition blend for forming an inner layer of the multi-layer sheath, including the substep of adding a detectable material to the first composition blend for facilitating external visualization of the multi-layer sheath; preparing a second composition blend for forming an outermost layer of the multi-layer sheath; combining the first and the second composition blends into a multi-layer pre-form; processing the multi-layer pre-form for producing coherent tubing, wherein the processing includes the substep of performing a reduced sintering process; and, forming a tip at one end of the coherent tubing using a thermal process, thereby producing the multi-layer sheath having the inner layer, the outermost layer, and the formed tip.

Still further aspects and advantages will become apparent from a consideration of the ensuing description and drawings.

BRIEF DESCRIPTION OF THE DRAWINGS

The invention will be better understood by reference to the following more detailed description and accompanying drawings in which.

DETAILED DESCRIPTION OF THE INVENTION

Figure 1:
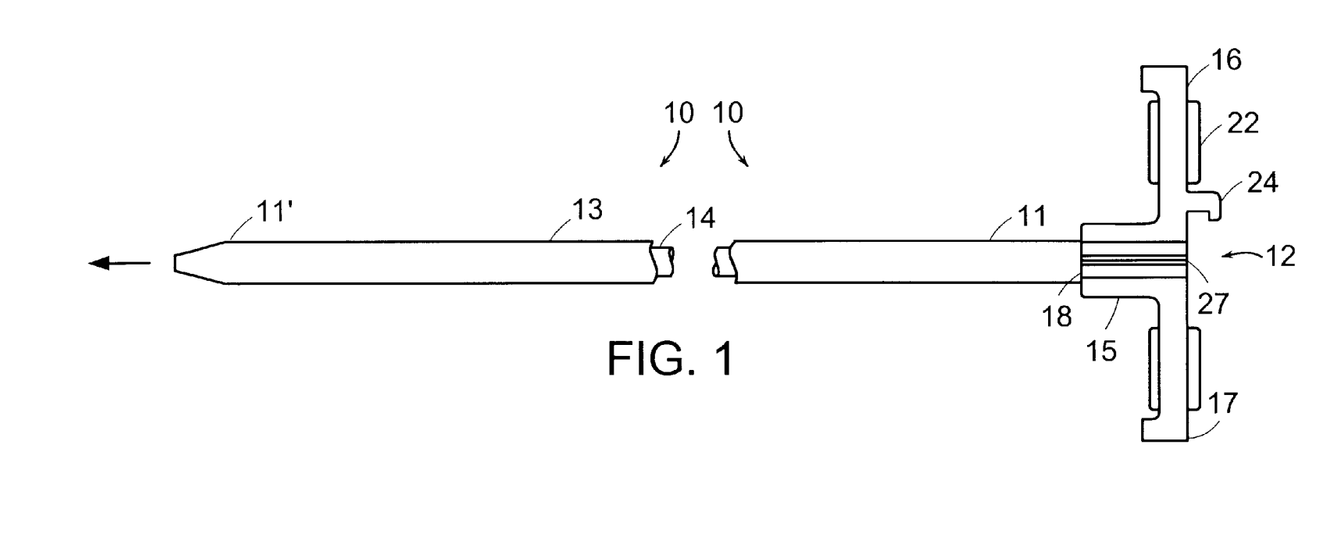
FIG. 1 is a side view of a medical introducer device including an introducer sheath with a formed tapered tip in accordance with the present invention.

FIG. 1 shows a side view of a medical introducer device 10, including an introducer sheath 11 with a formed tapered tip 11' in accordance with the present invention. The introducer sheath 11 includes a proximal end 27 and the formed tapered tip 11' at a distal end (not numbered). According to conventional practice, the proximal end 27 corresponds with the end of the introducer sheath 11 that is closer to attendant medical personnel manipulating the introducer device 10; and, the distal end of the introducer sheath 11 corresponds with the end of the introducer sheath 11 that is closer to the patient. Further, a bore 12 extends through the introducer sheath 11 between the proximal end 27 and the distal end of the introducer sheath 11.

In a preferred embodiment, the introducer sheath 11 is a multi-layer sheath, which includes, e.g., an inner layer 14 and an outer layer 13. Further, the inner layer 14 is preferably coextensive with the outer layer 13. A preferred method of manufacturing the introducer sheath 11 with the outer and inner layers 13 and 14 and the formed tapered tip 11' will be described in detail later in this specification.

The medical introducer device 10 further includes a hub unit 15, which is attached to the introducer sheath 11 at the proximal end 27. The hub unit 15 facilitates the longitudinal splitting of the introducer sheath 11. Specifically, the hub unit 15 substantially circumscribes the proximal end 27 of the introducer sheath 11 and includes a pair of longitudinal scores 18 on opposing sides of the hub unit 15. Accordingly, the hub unit 15 is in contact with a substantial circumferential surface area (not numbered) at the proximal end 27 of the introducer sheath 11, thereby defining break lines 21 (see FIG. 3) colinear with the pair of longitudinal scores 18 along which the introducer sheath 11 may be longitudinally split.

In addition, the medical introducer device 10 includes a plurality of wing portions 16 and 17 attached to the hub unit 15. The wing portions 16 and 17 further facilitate the longitudinal splitting of the introducer sheath 11. Specifically, the wing portions 16 and 17 are attached to the hub unit 15 so that they extend outwardly from the hub unit 15 in substantially diametrically opposed locations. Accordingly, the wing portions 16 and 17 provide areas (not numbered) upon which force may be manually applied for shearing and subsequently longitudinally splitting the introducer sheath 11, thereby peeling the introducer sheath 11 away from, e.g., a catheter disposed therein.

In the preferred embodiment, outer surfaces (not numbered) of the wing portions 16 and 17 include topography for aiding in the manipulation and overall handling of the medical introducer device 10. For example, the outer surfaces of the wing portions 16 and 17 preferably include raised gripping surfaces 22. Further, the wing portions 16 and 17 and/or the raised gripping surfaces 22 may be color-coded to designate particular dimensions of the introducer sheath 11, thereby enabling easy identification of a desired sheath size by the attendant medical personnel.

Also in the preferred embodiment, the introducer sheath 11 is adapted for snugly receiving a dilator assembly 19 (see FIG. 2), thereby facilitating entry of the medical introducer device 10 into, e.g., a vein or an artery of a patient. Accordingly, the wing portion 16 or 17 preferably includes a locking lip 24 for securing a flange 25 included on a handle 29 (see FIG. 2) of the dilator assembly 19, while the dilator assembly 19 is disposed in the introducer sheath 11.

Both the outer layer 13 and the inner layer 14 of the multi-layer introducer sheath 11 are preferably made of a flexible polymeric material, more preferably a polytetrafluoroethylene (PTFE) polymer such as TEFLON™ PTFE, which is sold by and a trademark of the E.I. DuPont Co., Inc., Wilmington, Del., USA. Another flexible, non-reactive material that is suitable for use in such medical devices includes fluorinated ethylene-propylene resin; however, other suitable materials may alternatively be used.

It is known that certain radiopaque materials that are added to the flexible polymeric material used to make introducer sheaths for facilitating x-ray or fluoroscopic visualization can cause discoloration of the introducer sheaths when forming the tapered tip using heat or RF energy. For this reason, the outer layer 13 of the introducer sheath 11 preferably includes a thermally stable, colored pigment, while the inner layer 14 of the introducer sheath preferably includes the added radiopaque material. As a result, any discoloration that may occur when forming the tapered tip 11' takes place only on the inner layer 14, not on the outer layer 13 of the introducer sheath 11.

This means that the outer layer 13 of the introducer sheath 11 can be made in a variety of different colors, e.g., white, blue, or any other thermally stable color, without sacrificing the radiopaque feature of the introducer sheath 11. In contrast, conventional introducer sheaths have traditionally been made only in dark colors, e.g., black, for hiding any discoloration resulting from tip-forming processes that use heat or RF energy. In the preferred embodiment, the outer layer 13 is produced in a lighter color, e.g., white, while the inner layer 14 is produced in a darker color, e.g., black, for easily distinguishing the outer and inner layers 13 and 14 of the introducer sheath 11.

Radiopaque materials that may be suitably added to the flexible polymeric material used to make the inner layer 14 of the introducer sheath 11 include barium sulfate, tungsten, bismuth sub-carbonate, and bismuth trioxide. Further, the amount of radiopaque material added to the inner layer 14 preferably ranges from about 1 or 2% to about 12% by weight. Such a configuration permits visualization of the introducer sheath 11 within a patient by x-ray or fluoroscopic procedures.

The hub unit 15 is preferably made of polypropylene. However, other suitable materials may alternatively be used.

Figure 2:
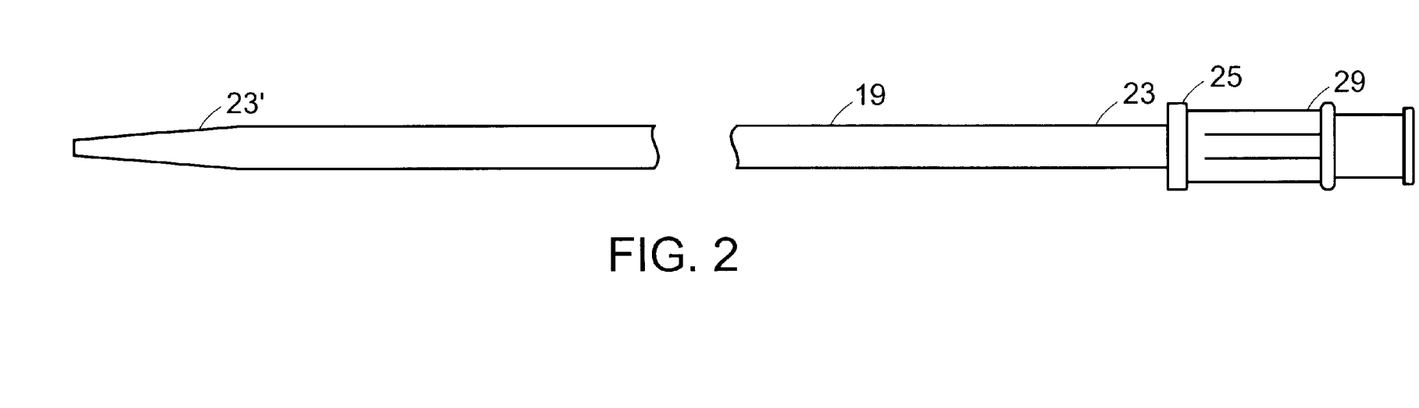
FIG. 2 is a side view of a dilator assembly for use with the medical introducer device of FIG. 1.

FIG. 2 shows a side view of the dilator assembly 19 for use with the medical introducer device 10. Specifically, the dilator assembly 19 includes an elongated portion 23 with the handle 29 attached thereto at a proximal end (not numbered); and, a tapered tip 23' at a distal end (not numbered). The dilator assembly 19 may further include a bore (not numbered) extending through the assembly 19 between the proximal and distal ends.

The dilator assembly 19 is preferably made of fluorinated ethylene-propylene resin. Another fluorinated resin that is suitable for use in such assemblies is, e.g., TEFLON™ PTFE; however, other suitable materials may alternatively be used.

It should be understood that the dilator assembly 19 is conventional and therefore known to those skilled in this art. Accordingly, specific structures used for implementing this component of the medical introducer device 10 are not critical to the present invention and may take different forms.

Figure 3:
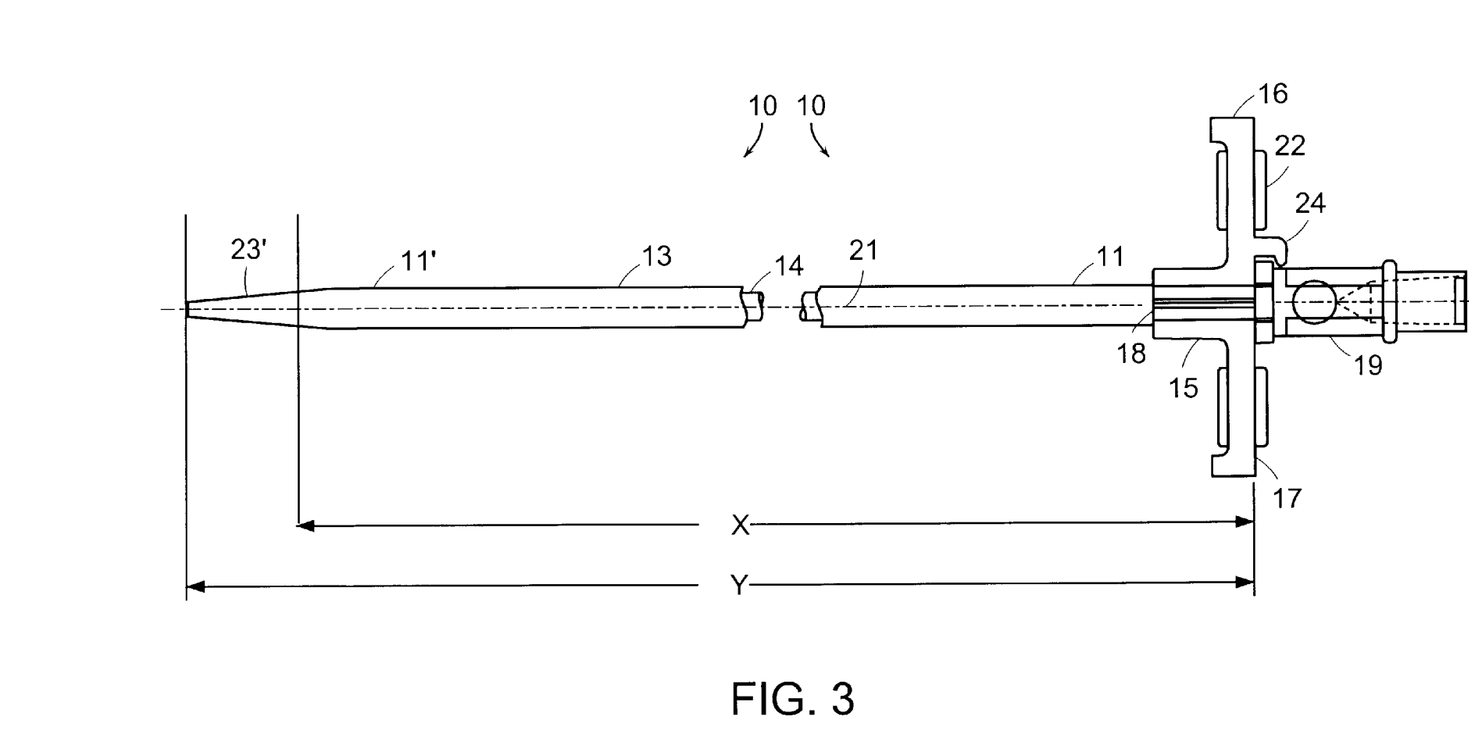
FIG. 3 is a partial cutaway, side view of the medical introducer device with the dilator assembly of FIG. 2 disposed in the introducer sheath.

FIG. 3 shows a partial cutaway, side view of the medical introducer device 10, with the dilator assembly 19 disposed in the introducer sheath 11. Specifically, FIG. 3 shows that the tapered tip 23' at the distal end of the dilator assembly 19 extends beyond the tapered tip 11' at the distal end of the introducer sheath 11. More specifically, the distal end of the dilator assembly 19 may extend beyond the distal end of the introducer sheath 11 by an amount ranging from about 1 inch to about 3 inches. Further, it was mentioned above that the introducer sheath 11 is preferably adapted for snugly receiving the dilator assembly 19, thereby facilitating entry of the medical introducer device 10 into the vasculatures of the patient. Accordingly, an opening (not numbered) near the tapered tip 11' at the distal end of the introducer sheath 11 is suitably formed for snugly receiving the elongated portion 23 of the dilator assembly 19.

Dimensions of the various components of the medical introducer device 10 can vary widely depending upon the intended application, and such dimensions can be readily determined by those skilled in the art based on the present disclosure. For example, the dilator assembly 19 would generally have outer diameters suitable for insertion into selected vasculatures of a patient; and, the introducer sheath 11 would have inner diameters sufficient for accommodating such an assembly 19. Further, the inner diameters of the introducer sheath 11 would be sufficient for subsequently accommodating a catheter or the like. In an illustrative embodiment, the introducer sheath 11 may be about 5 to about 6 inches in length, which is indicated as x in FIG. 3; and, the elongated portion 23 of the dilator assembly 19 may be about 7 to about 8 inches in length, which is indicated as y in FIG. 3.

It should be understood that the introducer sheath 11 and the dilator assembly 19 might be provided in other useful dimensions. However, in order to have a medical introducer device 10 that is most useful, the introducer sheath 11 and the dilator assembly 19 are preferably provided in dimensions for allowing an interference fit between the outer diameter of the elongated portion 23 of the dilator assembly 19 and the inner diameter of the tapered tip 11' of the introducer sheath 11. A preferred method of forming the tapered tip 11' to provide the interference fit between the outer diameter of the elongated portion 23 and the inner diameter of the tapered tip 11' will be described later in this specification.

Figure 4:
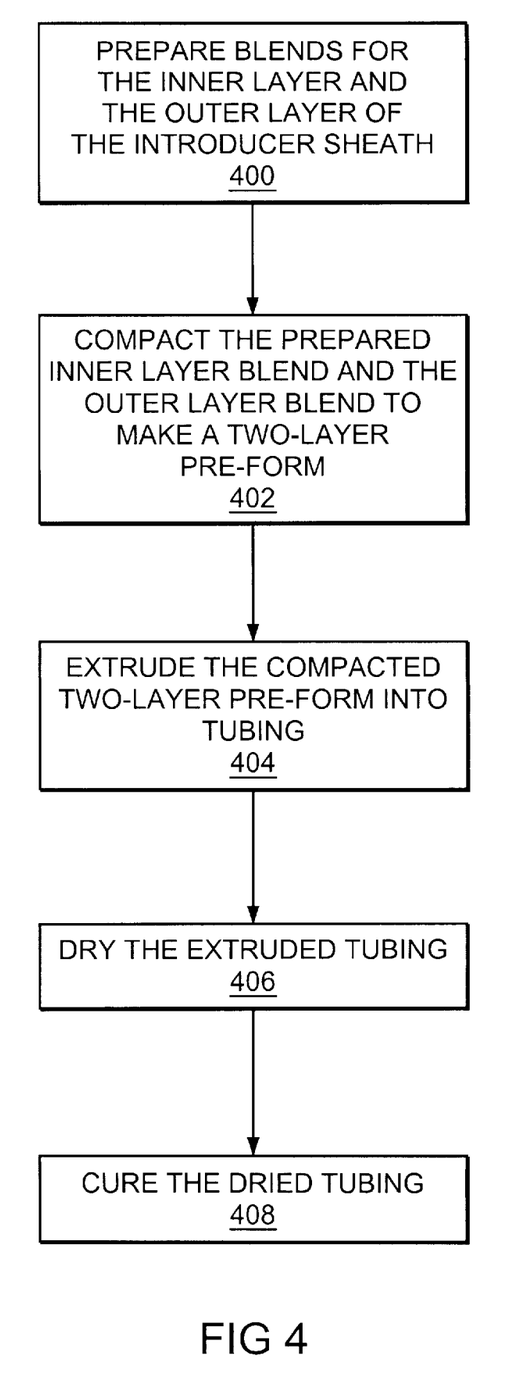
FIG. 4 is a flow chart showing steps performed when manufacturing tubing used for making the introducer sheath.

A preferred method of manufacturing tubing used for making the introducer sheath 11 will now be described with reference to the flow chart shown in FIG. 4. First, composition blends are prepared in block 400 for both the outer layer 13 and the inner layer 14 of the introducer sheath 11. Specifically, PTFE powder, a hydrocarbon lubricant, and a pigment are first mixed and blended for preparing the composition blend for the outer layer 13; and, this prepared composition blend is then aged for equilibrating the mixture. Further, PTFE powder, a hydrocarbon lubricant, and a radiopaque filler are similarly mixed and blended for preparing the composition blend for the inner layer 14; and, this prepared composition blend is then similarly aged for equilibrating the mixture.

Next, the composition blends for the outer and the inner layers 13 and 14 are compacted in block 402 for making a two-layer pre-form. Specifically, the composition blends are compacted for making the two-layer pre-form that can be easily inserted into a conventional extrusion machine (not shown). Further, the composition blends are compacted so that when the resulting pre-form is inserted into the extrusion machine, the composition blend for the outer layer 13 is positioned for forming an outer surface of extruded tubing and the composition blend for the inner layer 14 is positioned for forming an inner surface of the extruded tubing.

The compacted two-layer pre-form is then extruded in block 404 for forming the aforementioned tubing. Next, the extruded tubing is dried in block 406 for removing the hydrocarbon lubricant. Finally, the dried tubing is cured in block 408. Specifically, the steps of extruding, drying, and curing are preferably performed as part of a continuous process. For example, a length of tubing is formed by an extruder (not shown), and then conveyed through drying and curing ovens (not shown) at the line speed of the extruder. As a result, respective dwell times of the length of tubing within the drying and curing ovens can be easily determined by simply adjusting the line speed of the extruder. Although the two-layer tubing includes the outer layer 13 and the inner layer 14 as shown in FIG. 1, it should be understood that after the steps of extruding, drying, and curing are performed, the outer layer 13 and the inner layer 14 are inseparable.

Specifically, the line speed of the extruder, and therefore the respective dwell times within the drying and curing ovens, can be adjusted for obtaining optimal peel strength and/or other properties of the tubing. Specifically, the optimal peel strength typically varies with tubing size; and, TABLE 1 below shows preferred peel values for various tubing sizes.

TABLE 1

| FRENCH SIZE | PEEL VALUE | STANDARD DEVIATION |
| --- | --- | --- |
| 4F–8.5F | 0.85 | +/− 0.50 lbs. |
| 9F–13F | 1.25 | +/− 0.50 lbs. |
| 14F–18F | 1.80 | +/− 0.60 lbs. |

Accordingly, tubing used for making the introducer sheath 11 can be manufactured in accordance with the following illustrative example. First, the composition blend for the outer layer 13 is prepared by mixing and blending, for about 20 minutes, 25 lb. of PTFE fine powder, 5.1 lb. of a hydrocarbon lubricant, and 0.3 lb. of a white pigment in a conventional V-cone blender. Further, the composition blend for the inner layer 14 is prepared by similarly mixing and blending, for about 20 minutes, 25 lb. of PTFE fine powder, 4.5 lb. of a hydrocarbon lubricant, and 3.3 lb. of a radiopaque filler. Specifically, the PTFE fine powder may be TEFLON™ T6C PTFE; the hydrocarbon lubricant may be ISOPAR™ G lubricant, sold by Exxon Chemical Company, Houston, Tex., USA; the pigment may be a white pigment, e.g., 67% white pigment in ISOPAR™ G lubricant; and, the radiopaque filler may be 67% $Bi_2O_3$ in ISOPAR™ G lubricant. Both composition blends are then allowed to age for several hours until the mixtures are equilibrated.

Next, the composition blends are compacted for making the two-layer pre-form having a 2.5 inch outer diameter and a 0.625 inner diameter, wherein the composition blend for the outer layer 13 is at the outer diameter and the composition blend for the inner layer 14 is at the inner diameter.

The compacted two-layer pre-form is then extruded into tubing in a conventional manner using a die and a mandrel, thereby defining a 0.288 inch outer diameter and a 0.265 inch inner diameter. Next, the extruded tubing is dried in a conventional drying oven (not shown) for removing the hydrocarbon lubricant. The dried tubing is then cured. As explained above, the line speed of the extruder can be adjusted for setting respective dwell times within the drying and curing ovens, thereby obtaining the optimal peel strength and/or other properties of the tubing.

Although the PTFE thermoplastic materials included in the composition blends used to make the tubing generally have high melting temperatures, e.g., on the order of 350° C., the respective dwell times within the drying and curing ovens are preferably set for allowing a reduced sintering of the dried tubing. Finally, the cured tubing is cut into lengths of about 8.25 inches.

The tubing manufactured in accordance with this illustrative example has the following dimensions: 0.144 inch outer diameter, 0.125 inch inner diameter, 8.25 inch length, and 0.0095 inch wall thickness. Further, the color of the outside surface of the tubing is white, and the color of the inside surface of the tubing is yellow.

Figure 5:
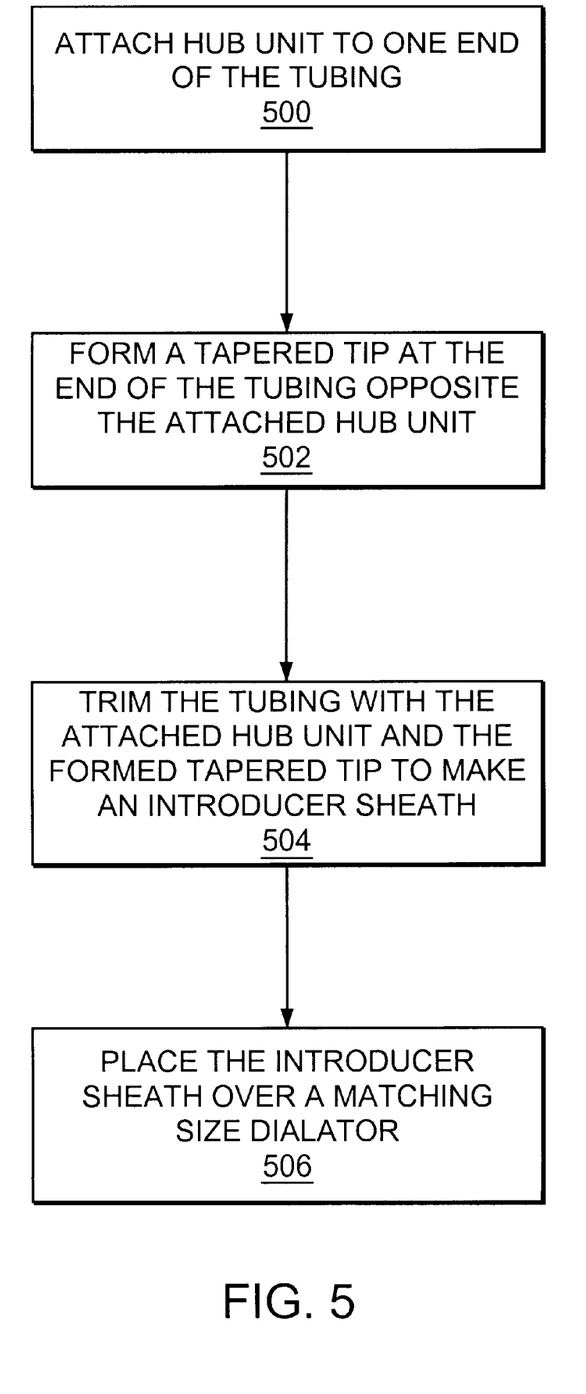
FIG. 5 is a flow chart showing steps performed when manufacturing the medical introducer device.

A preferred method of manufacturing the medical introducer device 10 using the tubing mentioned above will now be described with reference to the flow chart shown in FIG. 5. First, a hub unit 15 is attached in block 500 to one end of a cut length of tubing. In the preferred embodiment, the hub unit 15 is molded over the end of the cut length of tubing.

Next, the tapered tip 11' is formed in block 502 at the end of the cut length of tubing that is opposite the hub unit 15. The tapered tip 11' is preferably formed using, e.g., heat or RF energy. This is because the inner diameter of a RF energy-formed or heat-formed tapered tip typically decreases around a forming mandrel (not shown). Significantly, an introducer sheath having a tip formed in this manner has an interference fit between it and, e.g., a dilator assembly disposed therein. As a result, there is essentially no gap between the introducer sheath and the dilator assembly that might get hung-up and cause peel-back when the combination of the sheath and the dilator penetrate a patient's skin or arterial/venous wall, thereby virtually eliminating any serious trauma to the patient and damage to the introducer sheath.

It should be understood that the tapered tip 11' located at the end of the cut length of tubing opposite the hub unit 15 may be formed using heat or RF energy in any conventional manner. For example, the tapered tip 11' may be formed by applying heat to the tubing, and then stretching the tubing for forming the tapered tip 11' around a forming mandrel. Alternatively, a RF heated mold and a forming mandrel in combination may be used for forming the tapered tip 11'. Accordingly, the manner in which the tapered tip 11' is formed is also not critical to the present invention.

However, an important advantage is derived from the present invention in that the tapered tip 11' can be formed using, e.g., heat or RF energy without causing any visible discoloration to the cut length of tubing. This is because the radiopaque filler, which is typically the source of such discoloration, is added only to the composition blend used for forming the inner layer 14; the radiopaque filler is not added to the composition blend used for forming the outer layer 13. Even though the heat or RF energy used in the tip-forming process may cause some discoloration of the inner layer 14 due to the presence of the radiopaque filler in the inner layer 14, no discoloration of the outer layer 13 occurs. Any discoloration of the cut length of tubing resulting from the tip-forming process is therefore advantageously hidden from view.

In contrast, it is known by those skilled in this art that if radiopaque filler is added to a composition blend for a single layer pre-form, which is extruded, dried, and cured to form tubing, and a tapered end of the tubing is formed using, e.g., heat or RF energy, then brown and/or black colored spots will typically appear at the formed tapered end. Such spotting is generally unacceptable in tubing used for making medical introducer devices as described herein.

The cut length of tubing having the formed tapered tip 11' is then trimmed to a preferred length in block 504, thereby completing the manufacture of the introducer sheath 11. Finally, the introducer sheath 11 is placed over, e.g., a matching dilator assembly, thereby completing the manufacture of the medical introducer device 10.

Another important advantage derived from the present invention is that an introducer sheath that is made in accordance with the above-described methods can be easily longitudinally split or peeled. This is because the multi-layer tubing made according to the above-described method has a peel strength of about 1.56 lb., which is about 20% less than tubing made using conventional sintering methods. As a result, the hub unit 15 can be used for facilitating straight and even longitudinal splitting of the introducer sheath 11, thereby advantageously permitting the entire length of the introducer sheath 11 to be easily split.

The operation of the medical introducer device 10 will now be described in accordance with the following illustrative example, which describes the introduction of an ancillary medical device (not shown), e.g., a catheter into the vasculatures of a patient. First, a medical attendant inserts the dilator assembly 19 into the introducer sheath 11, thereby completing the medical introducer device 10. Next, the medical attendant uses the medical introducer device 10 to pierce and then dilate the vasculatures of a patient.

Following the dilation of the vasculatures of the patient, the medical attendant withdraws, e.g., the dilator assembly 19 from the introducer sheath 11. Next, the medical attendant inserts, e.g., the catheter through the bore 12 of the introducer sheath 11 to a desired target location in the vasculatures of the patient. The medical attendant then simultaneously applies outwardly cooperating forces to the wing portions 16 and 17 attached to the hub unit 15, thereby axially splitting the introducer sheath 11 along the longitudinal tear line 21 (see FIG. 3). Finally, the medical attendant removes the split introducer sheath 11 from the vasculatures of the patient, thereby leaving only the catheter in place within the vasculatures of the patient.

In accordance with another illustrative example, a guide wire (not shown) is used for aligning the medical introducer device 10 with a puncture site in the vasculatures of a patient. This method of operation is commonly known as the Seldinger technique. Specifically, a medical attendant first uses a needle (not shown) for penetrating the skin and arterial or venous wall of a patient, thereby forming the puncture site. Next, the medical attendant threads the guide wire through the needle and the puncture site and into the vasculatures of the patient. The medical attendant then removes the needle by sliding the needle over the free end of the guide wire, thereby leaving the guide wire in the vasculatures of the patient. Next, the medical attendant threads the free end of the guide wire through the medical introducer device 10; i.e., through the bore of the dilator assembly 19 disposed in the introducer sheath 11. In this way, the guide wire aligns the tapered tip 23' of the dilator assembly 19 disposed in the introducer sheath 11 with the puncture site, and guides the medical introducer device 10 into the vasculatures of the patient.

It follows from the above description that important benefits are derived from the methods of the present invention. For example, manufacturing tubing according to the method described above for use in an introducer sheath allows a formed tapered tip to be easily incorporated into the introducer sheath. Not only does such a formed tapered tip minimize trauma to a patient during a medical procedure, but it also minimizes the occurrence of peel-back. This reduces costs by minimizing the need for frequently discarding and replacing damaged sheath/dilator sets. Further, manufacturing tubing in accordance with the above-described methods allows a formed tapered tip to be incorporated into an introducer sheath having radiopaque filler with no visible discoloration of the introducer sheath. This is important for sterile medical introducer devices as described herein because any discoloration of the introducer sheath may be misidentified as contamination. Moreover, because no visible discoloration occurs after forming the tapered tip, the outer layer of the introducer sheath may be provided in a variety of colors including white, blue, or any other thermally stable color.

In addition, the above-described method simplifies the production of medical introducer devices made with preferred PTFE thermoplastic materials such as TEFLON™ PTFE, which typically has a high melting temperature. Further, the method as described herein can be used to make an introducer sheath having reduced peel strength. As a result, the introducer sheath can be easily split or peeled in a straight, even line along the entire length of the introducer sheath. In contrast, introducer sheaths made using conventional methods often have uneven and/or partial peel characteristics. Moreover, conventional introducer sheaths often produce stringers during peeling, thereby potentially contaminating the work area.

Having described one embodiment, numerous alternative embodiments or variations might be made. For example, it was described that the introducer sheath is adapted for receiving a dilator assembly, thereby facilitating entry of the sheath into the vasculatures of a patient. However, this was merely an illustrative example, and the sheath may alternatively be adapted for other uses. Specifically, the sheath may be adapted for use as a cannula; e.g., the sheath may be adapted for enclosing a trocar and allowing the escape of fluid from the patient in a conventional manner when the trocar is withdrawn.

In addition, the medical introducer device was described by describing the cooperation between an introducer sheath and a dilator assembly. However, this was also merely an illustrative example. The medical introducer device may alternatively include an over-the-needle (OTN) style introducer sheath, which is typically used for placing percutaneously inserted central catheters (PICC; not shown) into vasculatures of patients. Such OTN introducer sheaths are used with needle assemblies instead of dilator assemblies. The OTN introducer sheaths typically have lengths ranging from just under 1 inch to about 5 inches; and, the needle assembles used therewith typically have lengths ranging from just over 1 inch to about 6 inches. Further, the OTN introducer sheath preferably has a formed tip for allowing an interference fit between the inner diameter of the OTN sheath tip and the outer diameter of the needle assembly.

Further, in a typical method of operation, a medical attendant inserts the OTN introducer sheath with the needle assembly disposed therein through the skin and arterial or venous wall and into the vasculatures of a patient. The medical attendant then removes the needle assembly from the OTN introducer sheath, thereby leaving the OTN introducer sheath in the vasculatures of the patient. The medical attendant then inserts a PICC through the OTN introducer sheath and into the vasculatures of the patient. After the PICC has been properly placed into the vasculatures, the medical attendant withdraws the OTN introducer sheath from the vasculatures, splits and peels the OTN sheath, and removes the OTN sheath from the shaft of the PICC, thereby leaving the PICC in the vasculatures of the patient.

In addition, specific structures were described for the hub unit molded over the proximal end of the introducer sheath, and the wing portions attached to the hub unit. However, these were merely illustrative examples. Other structures may be used for facilitating straight and even splitting/peeling of the introducer sheath. Similarly, a specific structure was described for the dilator assembly used with the introducer sheath. However, this assembly is conventional and was also merely described as an illustrative example.

In addition, the introducer sheath according to the present invention was described as having an inner layer and an outer layer. However, this was merely an illustrative example. The introducer sheath may alternatively be made with more than 2 layers so long as the outermost layer does not include radiopaque filler, which may cause discoloration when forming a tapered tip using, e.g., heat or RF energy.

Therefore, the invention should be limited only by the spirit and scope of the appended claims.

What is claimed is:

1. A method of manufacturing a multi-layer sheath, comprising the steps of:
   (a) preparing a first composition blend for forming an inner layer of the multi-layer sheath;
   (b) preparing a second composition blend for forming an outermost layer of the multi-layer sheath;
   (c) combining the first and the second composition blends into a multi-layer pre-form;
   (d) processing the multi-layer pre-form for producing coherent tubing; and
   (e) forming a tip at one end of the coherent tubing using a thermal process, thereby producing the multi-layer sheath having the inner layer, the outermost layer, and the formed tip,
   wherein the preparing in step (a) includes the substep of adding a detectable material to the first composition blend for facilitating external visualization of the multi-layer sheath.

2. The method of manufacturing a multi-layer sheath as recited in claim 1,
   wherein the preparing in steps (a) and (b) includes adding a flexible polymeric material to both the first and the second composition blends.

3. The method of manufacturing a multi-layer sheath as recited in claim 2,
   wherein the flexible polymeric material includes a PTFE polymer.

4. The method of manufacturing a multi-layer sheath as recited in claim 3, wherein the PTFE polymer is TEFLON™ PTFE.

5. The method of manufacturing a multi-layer sheath as recited in claim 1,
   wherein the detectable material includes a radiopaque material for facilitating external visualization of the multi-layer sheath by x-ray or fluoroscopic procedures.

6. The method of manufacturing a multi-layer sheath as recited in claim 5,
   wherein the radiopaque material includes at least one of barium sulfate, tungsten, bismuth sub-carbonate, and bismuth trioxide.

7. The method of manufacturing a multi-layer sheath as recited in claim 1,
   wherein the preparing in step (b) includes the substep of adding a thermally stable pigment to the second composition blend.

8. The method of manufacturing a multi-layer sheath as recited in claim 1,
   wherein the preparing in steps (a) and (b) includes adding visibly distinct pigments to both the first and the second composition blends.

9. The method of manufacturing a multi-layer sheath as recited in claim 1, further including the step of equilibrating the first and the second composition blends before the combining in step (c).

10. The method of manufacturing a multi-layer sheath as recited in claim 1, wherein the processing in step (d) includes the substeps of extruding the combined composition blends for producing the coherent tubing, drying the coherent tubing, and curing the dried coherent tubing.

11. The method of manufacturing a multi-layer sheath as recited in claim 10, wherein the dried coherent tubing is cured using a reduced sintering process.

12. The method of manufacturing a multi-layer sheath as recited in claim 1, wherein the thermal process used in step (e) uses heat or RF energy.

13. A method of manufacturing a multi-layer sheath, comprising the steps of:

(a) preparing a first composition blend for forming an inner layer of the multi-layer sheath, including the substep of adding a detectable material to the first composition blend for facilitating external visualization of the multi-layer sheath;

(b) preparing a second composition blend for forming an outermost layer of the multi-layer sheath;

(c) combining the first and the second composition blends into a multi-layer pre-form;

(d) processing the multi-layer pre-form for producing coherent tubing, wherein the processing includes the substep of performing a reduced sintering process; and (e) forming a tip at one end of the coherent tubing using a thermal process, thereby producing the multi-layer sheath having the inner layer, the outermost layer, and the formed tip.

14. The method of manufacturing a multi-layer sheath as recited in claim 13, wherein the processing in step (d) includes the substeps of extruding the combined composition blends for producing the coherent tubing, drying the coherent tubing, and curing the dried coherent tubing using the reduced sintering process.

15. The method of manufacturing a multi-layer sheath as recited in claim 13, wherein the thermal process used in step (e) uses heat or RF energy.

16. The method of manufacturing a multi-layer sheath as recited in claim 13, wherein the detectable material includes a radiopaque material for facilitating external visualization of the multi-layer sheath by x-ray or fluoroscopic procedures.

* * * * *